United States Patent [19]

Bier

[11] Patent Number: 4,588,492
[45] Date of Patent: May 13, 1986

[54] ROTATING APPARATUS FOR ISOELECTRIC FOCUSING

[75] Inventor: Milan Bier, Tucson, Ariz.

[73] Assignee: University Patents, Inc., Westport, Conn.

[21] Appl. No.: 609,404

[22] Filed: May 7, 1984

[51] Int. Cl.⁴ .............................................. G01N 27/28
[52] U.S. Cl. .................. 204/301; 204/183.2; 204/182.3
[58] Field of Search .............. 204/299 R, 301, 180 R, 204/183.2, 182.3

[56] References Cited

U.S. PATENT DOCUMENTS

| | | | |
|---|---|---|---|
| 3,844,926 | 10/1974 | Smyth et al. | 204/299 R |
| 4,040,940 | 8/1977 | Bier | 204/299 R |
| 4,177,130 | 12/1979 | Herrmann et al. | 204/299 R |
| 4,204,929 | 5/1980 | Bier | 204/301 |
| 4,310,408 | 1/1982 | Rose et al. | 204/301 |
| 4,362,612 | 12/1982 | Bier | 204/301 |
| 4,465,583 | 8/1984 | Lovegrove | 204/299 R |

Primary Examiner—John F. Niebling
Assistant Examiner—B. J. Boggs, Jr.
Attorney, Agent, or Firm—David N. Koffsky

[57] ABSTRACT

This disclosure is directed to an isoelectric focusing apparatus, wherein stabilization of the fluid containing the isolated proteins is achieved by carrying out the separation in a rotating cylinder with the separation cavity of the cylinder being segmented by means of filter elements. The filter elements are constituted of a material offering some degree of resistance to fluid convection, but allowing relatively free and unhindered passage of current and transport of proteins. The combined effect of segmentation and rotation has been found to be superior to either segmentation or rotation alone in maintaining the stability of the migrated fractions.

8 Claims, 3 Drawing Figures

ROTATING APPARATUS FOR ISOELECTRIC FOCUSING

FIELD OF THE INVENTION

This invention relates to the separation and/or purification of biological materials and, more particularly, to apparatus for isoelectric focusing. The United States Government has rights in this invention pursuant to NASA contract NAS 8-32950.

BACKGROUND OF THE INVENTION

Isoelectric focusing ("IEF") also sometimes called electrofocusing, is an electrophoretic technique that is recognized as being a powerful method for the analysis and micropreparative separation and purification of various biological materials, including proteins, peptides, nucleic acids, viruses, and even some living cells of cell organelles. The principle of IEF is based on the fact that certain biomaterials, such as those listed above, are amphoteric in nature, i.e. are positively charged in acidic media and negatively charged in basic media. At a particular pH value, called the isoelectric point, they have a zero net charge. In other words, the isoelectric point is the pH value at which they undergo a reversal of net charge polarity. In a pH gradient such materials will migrate under the influence of a d.c. electric field until they reach the pH of their isoelectric point where they become immobilized by virtue of their zero net charge. Thus, they focus into narrow zones, defined by the pH of the medium and the electric field applied.

IEF techniques have been greatly advanced by the development of suitable buffer systems which form stable pH gradients in the electric field. Such buffers are usually composed of a random mixture of amphoteric substances having isoelectric points covering a wide spectrum of pH values. In the electric field, these components of the buffer mixture are also focused according to their isoelectric points, thereby establishing a stable pH gradient. A commercial mixture of such amphoteric substances called "Ampholine" is available from LKB Produkter AB, a Swedish Company. Other buffer systems are also compatible with IEF. The electric field in IEF thus has two simultaneous and overlapping functions; these being the establishment of the pH gradient and the focusing of the biomaterials to be separated. In terms of time sequence, the establishment of final focusing of the biomaterials cannot be achieved before a stable pH gradient is formed, i.e. before the components of the buffer mixture are focused.

IEF separation processes may be disturbed by bulk flow of liquid within an IEF apparatus. Two potential causes of bulk flow are electroosmosis and convection. If unchecked, these can disrupt the separation process by causing remixing of the separated fractions. Electroosmosis is caused by an electrical charge on the walls of the separation vessel, while convection is caused by local density differences arising from temperature and/or solute concentration gradients.

To prevent these disturbances, analytical IEF is mostly carried out in gels or packed granular support media. For preparative applications, free solutions are often preferred, as they simplify the collection of separated fractions. To control disruptive effects in free solution, several approaches have been previously used, whether for IEF or for more conventional forms of electrophoresis.

In vertical columns, density gradients have been very effective for fluid stabilization. These are formed by stratifying solutions of an electrically neutral solute, in order of decreasing density. While this system is quite effective for IEF, collection of the separated fractions is slow and cumbersome, a rapid drainage of the column frequently causing partial remixing of the separated fractions.

Shear effects have been utilized for fluid stabilization. The fluid is confined to a narrow space between two parallel plates as, for instance, in U.S. Pat. No. 4,310,408 to Rose, et al. This type of electrophoretic instrument has been utilized only rarely for IEF.

In horizontal columns, rotation around an horizontal axis has minimized convective disturbances by continuously changing the relationship of the fluid to the gravity vector. This mode of stabilization protects only against convective flows but not against electroosmosis. To minimize the same, anticonvective agents such as agarose or dextran are introduced either in the medium or as coatings on the column walls. Mainly, this mode of fluid stabilization is effective only in small bore tubes, as first shown by Hjerten (S. Hjerten: "Free Zone Electrophoresis", Almqvist and Wiksells, Uppsala, 1967) and collection of fractions is quite difficult (U.S. Pat. No. 4,040,940 to Bier).

A recirculating mode of focusing has been recently described in my previous U.S. Pat. Nos. 4,204,929 and 4,362,612 the disclosures of which are incorporated herein by reference. The solution to be fractionated is recirculated through a multichannel focusing cell and heat-exchange reservoir, by means of a multichannel peristaltic pump. While quite effective, relatively large volumes of fluid are necessary to prime the apparatus. In many research applications, where only small quantities of protein are available, this forces excessive dilution of the solution. Dilute protein solutions are notoriously less stable than more concentrated solutions. Experiments have shown that some recirculation or other form of mixing of the contents of each subcompartment is desirable, as separation in static fluids produces inferior results. Using colored proteins, such as hemoglobin, one notices a 'gravitational slumping' of the focused protein across the separating filter elements, if recirculation is interrupted.

Accordingly, an object of the present invention is to provide a novel method and means for stabilizing IEF columns against both electroosmosis and convection, which is applicable to both small and large processing volumes.

Another object of the invention is to provide means for preparative isoelectric focusing in free fluids, without the need for supporting materials, such as gels, powders, etc.

A further object of the invention is to provide means for rapid focusing of small volumes of proteinaceous liquid.

A still further object of the invention is to provide a means for simple and rapid collection of separated fractions.

SUMMARY OF THE INVENTION

The present invention deals with an apparatus for preparative fractionation of proteins by IEF, wherein stabilization of the fluid is achieved by carrying out the separation in a rotating elongated chamber with the separation cavity of the chamber being segmented by means of filter elements. The filter elements are constituted of a material offering some degree of resistance to fluid convection, but allowing relatively free and unhindered passage of current and transport of proteins. In IEF, proteins focus to narrow bands at pH values corresponding to their isoelectric points. In the invention, proteins migrate to one or more subcompartments, the contents of which are closest to their isoelectric point. The combined effect of segmentation and rotation has been found to be superior to either segmentation or rotation alone in maintaining the stability of the migrated fractions. In experiments segmentation alone has been found to be more effective than rotation, but does not fully protect against convecting slump of liquid fractions of higher density across several subcompartments. Only the combined effect of both segmentation and rotation is fully effective to produce satisfactory IEF separations.

The separation chamber is horizontally oriented with each subcompartment being accessible through a membrane or other access port. During focusing these access ports are sealed but for fraction collection they may be punctured or otherwise accessed by a matching array of needles connected to a vacuum. Simultaneous application of vacuum causes near instantaneous evacuation of the contents of all subcompartments into a matched set of test tubes.

DESCRIPTION OF A PREFERRED EMBODIMENT

Figure 1:
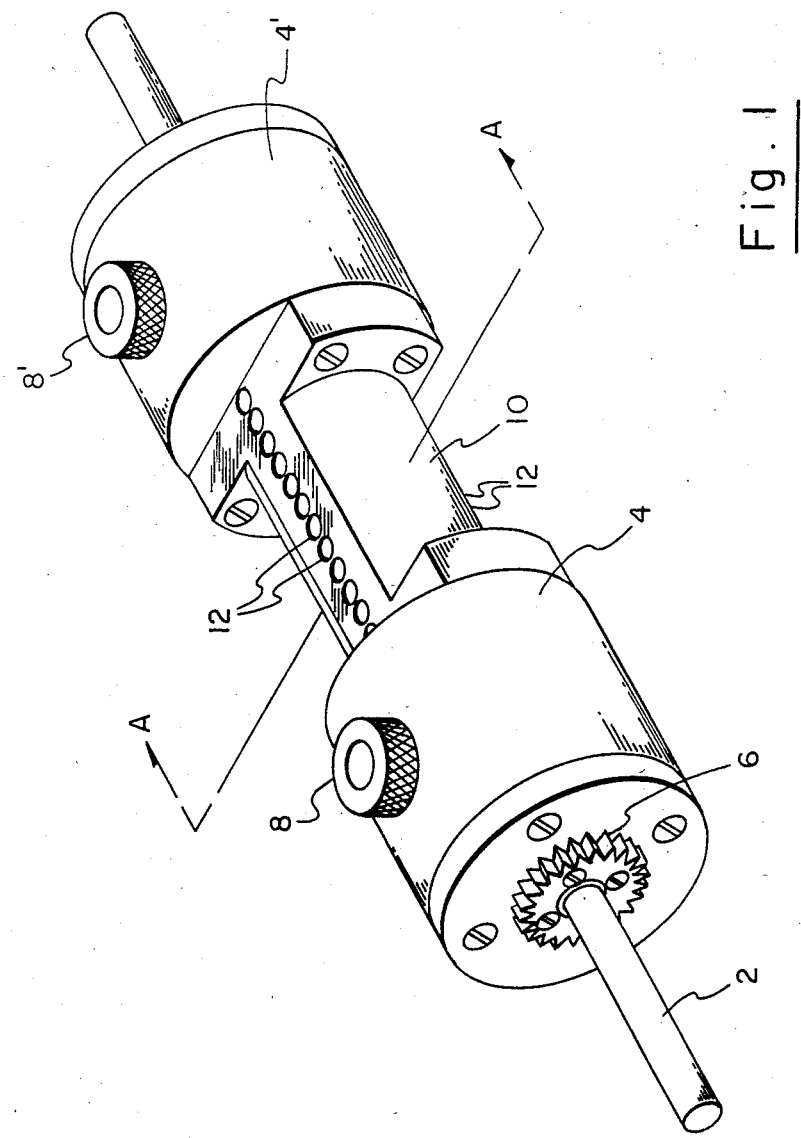
FIG. 1 is a perspective drawing of the rotating portion of the focusing apparatus.

Referring to FIG. 1, cooling tube 2 is central to the apparatus. Two electrode vessels 4 and 4' are symmetrically located at the ends of the apparatus. Gear 6, mounted on electrode vessel 4, is used to rotate the vessel about its long axis. It can also be used to transmit electric power to electrode vessel 4, in which case the opposing electrode vessel 4' is also provided with a matching gear. Electrolyte fluids are loaded through ports 8 and 8' for each of electrode vessels 4 and 4' respectively. The segmented separation portion 10 of the apparatus is provided with a set of inlet/outlet ports 12. While not shown, a flexible membrane is emplaced over ports 12 and is held in place by a removable frame.

Figure 2:
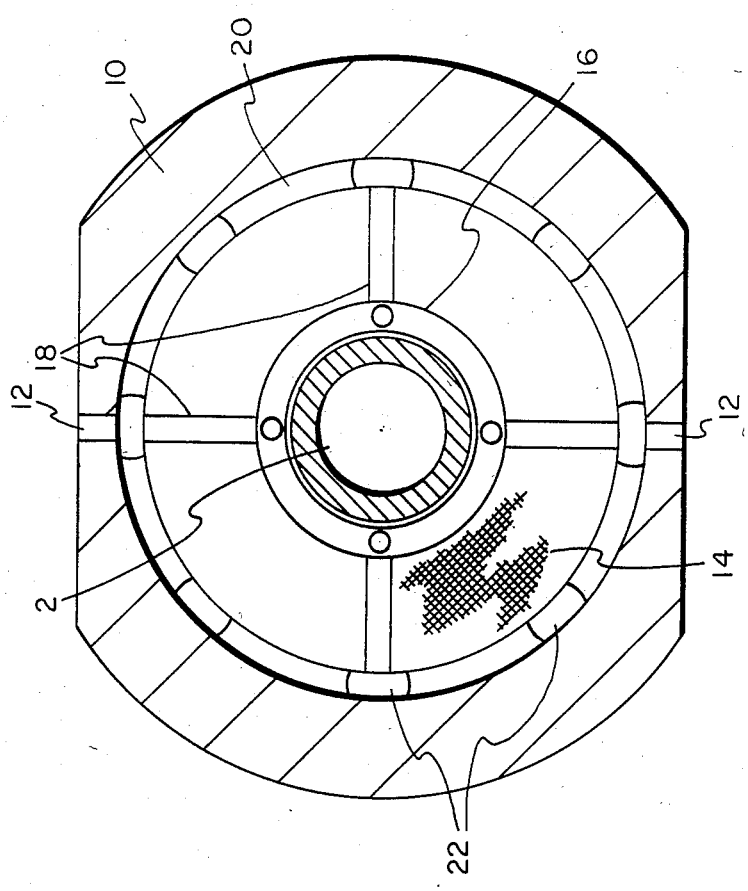
FIG. 2 shows a cross-section of the rotating portion along the line A—A in FIG. 1.

The cross-sectional view of the same apparatus taken along line A—A in FIG. 1 is shown in FIG. 2. Therein is shown internal cooling tube 2, external quasi-cylindrical body 10, inlet and outlet ports 12, and annular filter element 14, which is attached to a reinforcing annular frame 16. Frame 16 is provided with spokes 18 which connect to an outer ring 20. A plurality of sideways extending protrusions 22 are formed into ring 20 and provide sideways rigidity for the structure when a number of filter elements are mounted in a side-by-side arrangement.

Figure 3:
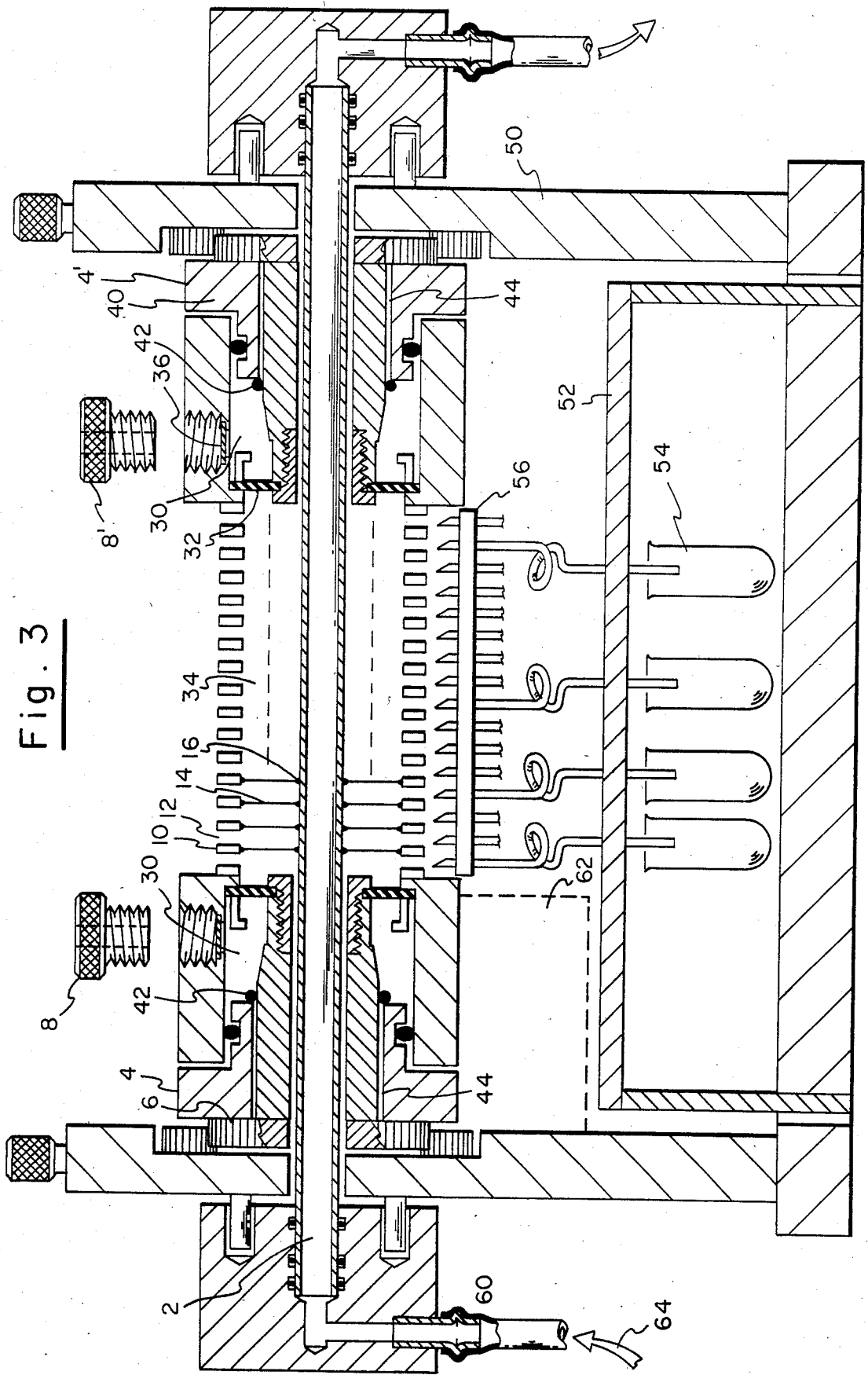
FIG. 3 is a schematic longitudinal cross-section of the rotating IEF apparatus shown in FIG. 1, as well as other accessory apparatus.

FIG. 3 is a schematic longitudinal cross-section of the invention, major portions of which are shown in FIGS. 1 and 2. Within each of electrode vessels 4 and 4' is an electrolyte chamber 30 which is separated by protein impermeable membrane 32 from the protein containing body 34 of the apparatus. After filling of chamber 30 with an appropriate electrolyte, hydrophobic membranes 36 are emplaced under ports 8 and 8' to allow venting of electrolytically generated gases without fluid spillage. Appropriate electrolytes are dilute phosphoric acid and sodium hydroxide.

Each electrode vessel is constructed of a nonconducting material, e.g. plastic. The inner portion 40 of each vessel has a platinum wire 42 which connects via conductor 44 to the respectively associated gear 6. A source of potential (not shown) is applied via carbon brushes to the gears to provide the necessary separating voltage to the apparatus.

The entire rotating structure is supported by frame 50, which also supports a fraction collecting vacuum box 52, fraction test tubes 54 and fraction collecting needle 56. Water circulation through the central cooling tube is indicated by arrow 64. Rotating seals 60 connect the rotating inner tube to the nonrotating refrigerant supply. A motor 62, located in the background, engages gear 6 and causes rotation.

The above described apparatus is only a preferred embodiment. Other versions are possible. For instance, the internal cooling column is not always necessary and cooling means can be provided to the outer shell of the apparatus. The design of electrode compartments can be varied, as well as the number and spacing of the annular segments (within wide limits). Two quite different instruments have been constructed. The first is a small apparatus without internal cooling, separation being conducted in a glass column of 1.8" length, ¼" I.D., subdivided into 14 subcompartments. Its total internal volume is less than 5 ml. The second apparatus is much larger, has an internal cooling tube, and is subdivided into 20 subcompartments. Separation is carried out in the annulus formed between the outer cylinder, 1.1" I.D. and the inner cooling tube, ⅜" O.D., the total length of the being 3.2". The contents of each subfraction is of the order of 2 ml, the total capacity of the apparatus being slightly over 40 ml. Rotational speed can be varied between 3 and 30 RPM. The performance of both of these instruments was very similar, except for the obvious difference of volume capacity. Calculations show that such instruments can be conveniently designed to handle batches of from 5 ml to 200 ml, or even larger. The capacity of 40 ml of the described apparatus seems adequate for much of biomedical research.

In this preferred version the central cooling tube is made of glass, the bulk of the rest of the apparatus being made of plexiglass or other similar plastics. Hydrophobic membranes 36 are made of microporous teflon, and ion exchange or dialyzing membranes (e.g. regenerated cellulose) are used for the protein impermeable membranes 32. Filter elements 14 are made of fine porosity monofilament screens with a preferred nominal porosity of between 1 and 20 microns. The gears 6, on either side of the column, are made of stainless steel and carry the focusing current to platinum electrodes 42. Alternatively, other means of current transmission can be provided. The electrolytes preferably used in focusing are dilute solutions of phosphoric acid and sodium hydroxide, the required volume being less than 5 ml each. Other electrolytes can be used as well. The pH gradient in the fractionation column can be established as customary in IEF, using a variety of carrier ampholytes well known in the art. Cooling of the apparatus is through recirculation of a cold brine through the internal tube. In addition, for some fractionations, the whole apparatus can be placed into a refrigerator.

The apparatus is filled manually by closing one set of ports 12 and introducing the fluid to be fractionated by means of a syringe through the other set of ports. Complete filling of all subcompartments is not essential, as the apparatus performs equally well when full or when air bubbles or pockets of air are left in some or all of the subcompartments. Before the rotation is initiated, the inlet ports are closed. A clamp or other means may be used to reinforce the closure membranes during rotation.

The progress of focusing can be observed by decrease of current at a constant voltage. The most advantageous mode of operation of a focusing instrument is at constant power. During such a run, the electric field may start initially at about 5 or 10 volts/cm and gradually increase up to 100 or 200 volts/cm, as the conductivity of the focused medium decreases.

For collection of separated fractions, one set of ports 12 of the apparatus has to be brought into alignment with the needle array 56. This is accomplished automatically, by means of a microswitch (not shown) which governs the positioning of the rotating column every time the current is interrupted. The needle array is cantilevered. When fraction collection is desired, the top set of ports is opened by removing the covering membrane, and the lever holding the needle array depressed. This forces the needles to penetrate the membrane covering the lower set of ports 12. The contents of all subcompartments are instantaneously sucked into their respective test tubes by the vacuum action.

It should be pointed out that unidirectional rotation is not necessary. Comparable results have been obtained by just imposing a rocking motion onto the separation columns, the rotation in each direction being between 180 and 360 degrees. In fact, the use of a rocking motion simplifies somewhat the construction of the apparatus as rotating seals can be avoided and flexible tubing used for the circulation of the cooling fluid.

EXAMPLE

The following is a typical mode of operation of the apparatus. Fifty milligrams each of two proteins, human serum albumin and hemoglobin, were added to 45 ml of a 1% solution of Ampholine (Trademark of the commercial carrier ampholyte for focusing, LKB Corp., Rockville, Md.), and filled by syringe into the apparatus described in FIGS. 1 to 3. The focusing was initiated at 100 Volts, which was gradually increased to 300 Volts during the three hours of focusing. Fractionation could be followed visually, as hemoglobin is naturally red and the albumin was stained blue by the addition of bromphenol blue dye. These two colorations were clearly visible through the plastic body of the apparatus, the blue albumin occupying four subcompartments closer to the anodic side of the apparatus, hemoglobin occupying three subcompartments closer to the cathodic side. These two regions were separated by eight subcompartments devoid of any proteins. This was confirmed by fraction collection, each of the proteins being collected in the test tube corresponding to its subcompartment in the focusing apparatus.

1. In an isoelectric focusing apparatus including an elongated separation chamber bounded by electrode chambers across which a voltage may be applied, said chambers adapted to be filled with an electrolyte, the improvement comprising;
   filter means dividing said separation chamber into a plurality of contiguous chambers, each of said filter means adapted to enable the ready passage therethrough of proteins to be focused;
   access means communicating with each said contiguous chamber;
   means for introducing a fluid to be fractionated into said contiguous chambers;
   means for imparting to said separation chamber movement about its elongated dimension; and
   means for collecting individually and substantially simultaneously after separation, the contents of each said contiguous chamber via said access means.

2. The invention as recited in claim 1 wherein said separation chamber is cylindrical, oriented in a horizontal mode and is mounted for rotational movement.

3. The invention as recited in claim 2 wherein said filter means create a plurality of annular chambers within said cylindrical separation chamber.

4. The invention as recited in claim 3 wherein opposing entry ports through the wall of said separation chamber communicate with each said annular chamber.

5. The invention as recited in claim 4 further including cooling means cooperating with said apparatus.

6. The invention as recited in claim 5 wherein said cooling means comprises a cooling tube within said elongated separation chamber.

7. The invention as recited in claim 2 wherein said rotative movement is undirectional and in the range of 3 to 30 revolutions per minute.

8. The invention as recited in claim 2 where in said rotative movement is reversing in direction between 3 and 30 times per minute said reversal of rotation inducing a rocking motion with an angle of at least 180 degrees.

* * * * *